US00PP28921P2

(12) United States Plant Patent
Chen

(10) Patent No.: US PP28,921 P2
(45) Date of Patent: Jan. 30, 2018

(54) ***ANTHURIUM* PLANT NAMED 'RYN2010083'**

(50) Latin Name: *Anthurium andreanum*
Varietal Denomination: RYN2010083

(71) Applicant: DUMMEN GROUP B.V., De Lier (NL)

(72) Inventor: Meng Chen, De Lier (NL)

(73) Assignee: Dümmen Group B.V., De Lier (NL)

( * ) Notice: Subject to any disclaimer, the term of this patent is extended or adjusted under 35 U.S.C. 154(b) by 0 days.

(21) Appl. No.: 15/530,035

(22) Filed: Nov. 22, 2016

(51) Int. Cl.
*A01H 5/02* (2006.01)

(52) U.S. Cl.
USPC ..... Plt./365

(58) Field of Classification Search
USPC ..... Plt./365, 369
CPC ..... A01H 5/02
See application file for complete search history.

*Primary Examiner* — Kent L Bell
(74) *Attorney, Agent, or Firm* — C. A. Whealy

(57) ABSTRACT

A new and distinct cultivar of *Anthurium* plant named 'RYN2010083', characterized by its compact, upright, outwardly arching and uniform plant habit; freely clumping growth habit; bushy and dense plants; glossy dark green-colored leaves; early and freely flowering habit; large red-colored spathes that are positioned at the center of the plant, above and beyond the foliage on strong and erect scapes; and good inflorescence longevity.

1 Drawing Sheet

Botanical designation: *Anthurium andreanum.*
Cultivar denomination: 'RYN2010083'.

BACKGROUND OF THE INVENTION

The present invention relates to a new and distinct cultivar of *Anthurium* plant, botanically known as *Anthurium andreanum* and hereinafter referred to by the name 'RYN2010083'.

The new *Anthurium* plant is a product of a controlled breeding program conducted by the Inventor in De Lier, The Netherlands. The objective of the breeding program is to create new compact *Anthurium* plants that flower early and have large attractive inflorescences.

The new *Anthurium* plant originated from a cross-pollination made by the Inventor in mid-October, 2008 in De Lier, The Netherlands of a proprietary selection of *Anthurium andreanum* identified as code number AT05-000059-011, not patented, as the female, or seed, parent with a proprietary selection of *Anthurium andreanum* identified as code number AT90-000114-002, not patented, as the male, or pollen, parent. The new *Anthurium* was discovered and selected by the Inventor as a single flowering plant within the progeny of the stated cross-pollination in a controlled greenhouse environment in De Lier, The Netherlands in early July, 2010.

Asexual reproduction of the new *Anthurium* plant by tissue culture in a controlled environment in Lochristi, Belgium since late November, 2010 has shown that the unique features of this new *Anthurium* are stable and reproduced true to type in successive generations of asexual reproduction.

SUMMARY OF THE INVENTION

Plants of the new *Anthurium* have not been observed under all possible combinations of environmental conditions and cultural practices. The phenotype may vary somewhat with variations in environment conditions such as temperature and light intensity, without, however, any variance in genotype.

The following traits have been repeatedly observed and are determined to be the unique characteristics of 'RYN2010083'. These characteristics in combination distinguish 'RYN2010083' as a new and distinct *Anthurium* plant:

1. Compact, upright, outwardly arching and uniform plant habit.
2. Freely clumping growth habit; bushy and dense plants.
3. Glossy dark green-colored leaves.
4. Early and freely flowering habit.
5. Large red-colored spathes that are positioned at the center of the plant, above and beyond the foliage on strong and erect scapes.
6. Good inflorescence longevity.

Plants of the new *Anthurium* differ from plants of the female parent selection in the following characteristics:

1. Plants of the new *Anthurium* are more compact than plants of the female parent selection.
2. Plants of the new *Anthurium* have smaller leaves than plants of the female parent selection.
3. Leaves of plants of the new *Anthurium* are darker green in color than leaves of plants of the female parent selection.

Plants of the new *Anthurium* differ from plants of the male parent selection in the following characteristics:

1. Plants of the new *Anthurium* are denser and bushier than plants of the male parent selection.
2. Plants of the new *Anthurium* have smaller spathes than plants of the male parent selection.
3. Plants of the new *Anthurium* and the male parent selection differ in spathe color as plants of the male parent selection have orange-colored spathes.

Plants of the new *Anthurium* can also be compared to plants of *Anthurium andreanum* 'Red King', disclosed in U.S. Plant Pat. No. 13,381. In side-by-side comparisons, plants of the new *Anthurium* differ from plants of 'Red King' in the following characteristics:

1. Plants of the new *Anthurium* are more compact and denser than plants of 'Red King'.
2. Plants of the new *Anthurium* have smaller and darker green-colored leaves than plants of 'Red King'.
3. Plants of the new *Anthurium* have narrower spathes than plants of 'Red King'.

BRIEF DESCRIPTION OF THE PHOTOGRAPH

The accompanying photograph illustrates the overall appearance of the new *Anthurium*. The photograph shows the colors as true as it is reasonably possible to obtain in colored reproductions of this type. Colors in the photograph may differ slightly from the color values cited in the detailed botanical description which accurately describe the colors of the new *Anthurium*. The photograph is a side perspective view of a typical plant of 'RYN2010083' grown in a container.

DETAILED BOTANICAL DESCRIPTION

The aforementioned photograph and following observations and measurements describe plants grown in 14-cm containers in De Lier, The Netherlands during the late summer in a glass-covered greenhouse. Plants were grown under conditions and practices which approximate those generally used in commercial *Anthurium* production. During the production of the plants, day temperatures ranged from about 22° C. to 25° C., night temperatures ranged from about 17° C. to 20° C. and light levels ranged from 1.6 to 2 klux. Plants were 30 weeks old when the photographs and the detailed description were taken. In the following description, color references are made to The Royal Horticultural Society Colour Chart, 2001 Edition, except where general terms of ordinary dictionary significance are used.

Botanical classification: *Anthurium andreanum* 'RYN2010083'.

Parentage:

*Female, or seed, parent.*—Proprietary selection of *Anthurium andreanum* identified as code number AT05-000059-011, not patented.

*Male, or pollen, parent.*—Proprietary selection of *Anthurium andreanum* identified as code number AT90-000114-002, not patented.

Propagation:

*Type.*—By tissue culture.

*Time to initiate roots, summer.*—About two weeks at temperatures about 20° C.

*Time to initiate roots, winter.*—About three weeks at temperatures about 15° C.

*Time to produce a rooted young plant, summer.*—About 70 days at temperatures about 20° C.

*Time to produce a rooted young plant, winter.*—About 91 days at temperatures about 15° C.

*Root description.*—Medium in thickness, fleshy; typically pinkish in color, actual color of the roots is dependent on substrate composition, water quality, fertilizer type and formulation, substrate temperature and physiological age of roots.

*Rooting habit.*—Moderately freely branching, medium density.

Plant description:

*Plant shape.*—Compact, upright and outwardly spreading plant habit; broad inverted triangle; symmetrical.

*Growth habit.*—Freely clumping, bushy and dense; vigorous growth habit.

*Plant height, from soil level to top of leaf plane.*—About 20 cm.

*Plant height, from soil level to top of inflorescences.*—About 30 cm.

*Plant diameter or spread.*—About 40 cm.

Leaf description:

*Arrangement.*—Alternate; simple.

*Length.*—About 20 cm.

*Width.*—About 12 cm.

*Shape.*—Cordate.

*Apex.*—Acute.

*Base.*—Auriculate.

*Margin.*—Entire.

*Texture and luster, upper and lower surfaces.*—Smooth, glabrous; leathery; glossy.

*Venation pattern.*—Pinnate.

*Color.*—Developing leaves, upper surface: Close to 136A. Developing leaves, lower surface: Close to 137C. Fully expanded leaves, upper surface: Close to 131A; venation, close to 138B. Fully expanded leaves, lower surface: Close to 137C; venation, close to 138B.

*Petioles.*—Length: About 15 cm. Diameter, just below geniculum: About 4 mm. Diameter, at plant base: About 4 mm. Strength: Strong. Texture and luster, upper and lower surfaces: Smooth, glabrous; moderately glossy. Color, upper and lower surfaces: Close to 137B. Geniculum length: About 1 cm. Geniculum diameter: About 4 mm. Geniculum texture and luster: Smooth, glabrous; moderately glossy. Geniculum color, upper and lower surfaces: Close to 137B.

Inflorescence description:

*Inflorescence arrangement and flowering habit.*—Spathes with spadices held above and beyond the foliage on strong and erect scapes; flowering structures arise from leaf axils; freely and continuous flowering year-round in The Netherlands; typically about seven open inflorescences per plant at one time.

*Fragrance.*—None detected.

*Inflorescence longevity.*—Inflorescences last about six to twelve weeks on the plant; inflorescences last about 20 days as a cut flower; inflorescences persistent.

*Spathes.*—Length: About 13 cm. Width: About 11 cm. Shape: Ovate. Apex: Acuminate. Base: Truncate. Margin: Entire. Texture and luster, upper and lower surfaces: Smooth, glabrous; leathery; glossy. Color: When developing, front and rear surfaces: Close to 46A. Fully developed, front surface: Close to 45A; color does not change with development. Fully developed, rear surface: Close to 46B; color does not change with development.

*Spadix.*—Length: About 5 cm. Diameter: About 8 mm. Shape: Columnar, tapering towards the apex; apex, obtuse; base, obtuse; cross-section, rounded. Aspect: Mostly erect. Color: Immature: Close to 19D. Mature: Close to 146C. Flowers: Quantity per spadix: Numerous, about 400. Shape: Rounded. Height: About 1 mm. Diameter: About 1 mm. Color, immature: Close to 19D. Color, mature: Close to 146C. Pollen amount: Scarce. Pollen color: Close to 158B.

Stigma shape: Ovoid. Stigma color: Close to 155D. Ovary color: Close to 155D.

*Scape*.—Length: About 25 cm. Diameter: About 4 mm. Strength: Strong. Aspect: Erect to slightly outwardly slanted. Color: Close to 137B.

*Seed and fruit*.—Seed and fruit development has not been observed on plants of the new *Anthurium*.

Pathogen & pest resistance: Plants of the new *Anthurium* have not been observed to be resistant to pathogens or pests common to *Anthurium* plants.

Temperature tolerance: Plants of the new *Anthurium* have been observed to be tolerant to temperatures ranging from about 15° C. to about 35° C.

It is claimed:

1. A new and distinct *Anthurium* plant named 'RYN2010083' as illustrated and described.

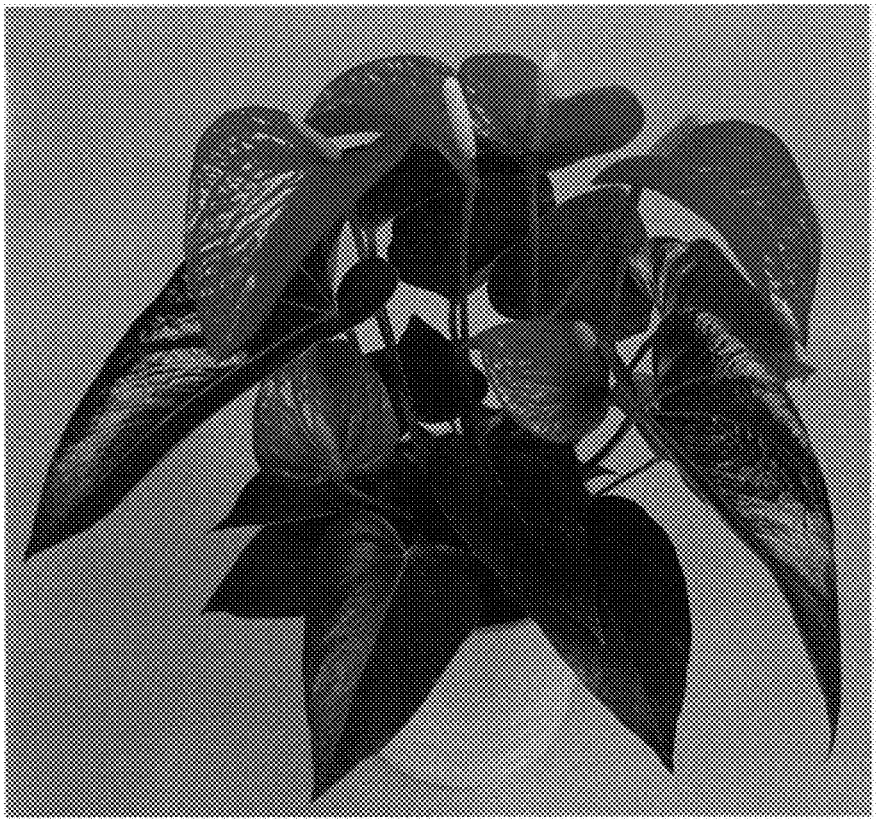

* * * * *